(12) United States Patent
Eschenhagen et al.

(10) Patent No.: US 10,172,712 B2
(45) Date of Patent: Jan. 8, 2019

(54) METHOD AND APPARATUS FOR MEASURING CONTRACTION CHARACTERISTICS OF ENGINEERED HEART TISSUE CONSTRUCTS

(71) Applicants: Universitätsklinikum Hamburg-Eppendorf, Hamburg (DE); Technische Universität Hamburg-Harburg, Hamburg (DE)

(72) Inventors: Thomas Eschenhagen, Hamburg (DE); Ingra Mannhardt, Hamburg (DE); Jörg Müller, Buchholz (DE); Christoph Warncke, Hamburg (DE); Jördis Weiser, Preetz (DE)

(73) Assignees: Universitätsklinikum Hamburg-Eppendorf, Hamburg (DE); Technische Universität Hamburg-Harburg, Hamburg (DE)

( * ) Notice: Subject to any disclaimer, the term of this patent is extended or adjusted under 35 U.S.C. 154(b) by 0 days.

(21) Appl. No.: 14/780,199

(22) PCT Filed: Mar. 25, 2014

(86) PCT No.: PCT/EP2014/055981
§ 371 (c)(1),
(2) Date: Sep. 25, 2015

(87) PCT Pub. No.: WO2014/154704
PCT Pub. Date: Oct. 2, 2014

(65) Prior Publication Data
US 2016/0030177 A1    Feb. 4, 2016

(30) Foreign Application Priority Data
Mar. 25, 2013 (EP) .................................... 13160816

(51) Int. Cl.
| | | |
|---|---|---|
| *A61F 2/24* | (2006.01) | |
| *A61B 5/11* | (2006.01) | |
| *G09B 23/30* | (2006.01) | |

(52) U.S. Cl.
CPC .......... *A61F 2/2472* (2013.01); *A61B 5/1108* (2013.01); *G09B 23/30* (2013.01);
(Continued)

(58) Field of Classification Search
CPC ............. A61F 2/2472; A61F 2240/008; A61B 5/1108; A61B 2562/0252; A61B 2562/0261; A61B 2562/028; G09B 23/30
(Continued)

(56) References Cited

U.S. PATENT DOCUMENTS

2003/0091979 A1* 5/2003 Eschenhagen ......... C12M 21/08
435/4
2006/0105357 A1 5/2006 Benesch et al.

FOREIGN PATENT DOCUMENTS

| EP | 1783206 A1 | 5/2007 |
|---|---|---|
| EP | 1920789 A1 | 5/2008 |
| WO | WO-06102890 A1 | 10/2006 |

OTHER PUBLICATIONS

European Application Serial No. 13160816.8, Extended European Search Report dated Aug. 23, 2013, 9 pgs.
(Continued)

*Primary Examiner* — Lisa Caputo
*Assistant Examiner* — Nathaniel T Woodward
(74) *Attorney, Agent, or Firm* — Schwegman Lundberg & Woessner, P.A.

(57) ABSTRACT

The invention is directed to a novel method for measuring contraction characteristics of engineered heart tissue constructs (16) which is based on the mechanical coupling of the construct (16) to a support element (8) which comprises or
(Continued)

is mechanically coupled to a piezoelectric element (10). An apparatus (1) for carrying out the method of the invention is also provided.

13 Claims, 2 Drawing Sheets

(52) U.S. Cl.
CPC . *A61B 2562/028* (2013.01); *A61B 2562/0252* (2013.01); *A61B 2562/0261* (2013.01); *A61F 2240/008* (2013.01)

(58) Field of Classification Search
USPC ........................................................ 73/866.4
See application file for complete search history.

(56) References Cited

OTHER PUBLICATIONS

International Application Serial No. PCT/EP2014/055981, International Search Report dated Jul. 18, 2014, 4 pgs.
International Application Serial No. PCT/EP2014/055981, Written Opinion dated Jul. 18, 2014, 7 pgs.
Bian, Weining, et al., "Mesoscopic Hydrogel Molding to Control the 3d Geometry of Bioartificial Muscle Tissues", Nature Protocols, 4, (2009), 1522-1534.
Carrier, Rebecca L, et al., "Cardiac Tissue Engineering: Cell Seeding, Cultivation Parameters, and Tissue Construct Characterization", Biotechnology and Bioengineering, 64, (1999), 580-589.
Engelmayr, George, et al., "Accordion-Like Honeycombs for Tissue Engineering of Cardiac Anisotropy", Nature Materials, 7, (2008), 1003-1010.
Eschenhagen, Thomas, et al., "Three-Dimensional Reconstitution of Embryonic Cardiomyocytes in A Collagen Matrix: A New Heart Muscle Model System", FASEB Journal, 11(8), (1997), 683-694.
Eshenhagen, T., et al., "Engineering Myocardial Tissue", Circ. Res.. 97(12), (2005), 1220-1231.
Hansen, Arne, et al., "Development of a Drug Screening Platform Based on Engineered Heart Tissue", Circulation Research 107 (1), (2010), 35-44.
Huang, Yen-Chih, et al., "Contractile Three-Dimensional Bioengineered Heart Muscle for Myocardial Regeneration", Journal of Biomedical Materials Research Part A, 80, (2007), 719-731.
Leor, Jonathan, et al., "Bioengineered Cardiac Grafts a New Approach to Repair the Infarcted Myocardium?", Circulation, 102 (19 Suppl 3), (2000), III-56-III-61.
Li, Ren-Ke, et al., "Construction of a Bioengineered Cardiac Graft", The Journal of Thoracic and Cardiovascular Surgery, 119, (2000), 368-375.
Naito, et al., "Optimizing Engineered Heart Tissue for Therapeutic Applications as Surrogate Heart Muscle", Circulation 114 (1 Suppl), (2006), I-72-I-78.
Ott, H. C, et al., "Perfusion-Decellularized Matrix: Using Nature's Platform to Engineer a Bioartificial Heart", Nat Med., 14(2), (Feb. 1, 2008), 213-221.
Radisic, M, et al., "Functional Assembly of Engineered Myocardium by Electrical Stimulation of Cardiac Myocytes Cultured on Scaffolds", Proc Natl Acad Sci U S A., 101(52), (Dec. 28, 2004), 18129-18134.
Schaaf, Sebastian, et al., "Human Engineered Heart Tissue as a Versatile Tool in Basic Research and Preclinical Toxicology", PLoS One 6(10), (2011), e26397.
Shimizu, T., et al., "Fabrication of Pulsatile Cardiac Tissue Grafts Using a Novel 3-Dimensional Cell Sheet Manipulation Technique and Temperature-Responsive Cell Culture Surfaces", Circ Res., 90(3). (Feb. 22, 2002), e40-e48.
Zimmerman, W. H., et al., "Tissue Engineering of A Differentiated Cardiac Muscle Construct", Circulation Res., 90(2), (2002), 223-30.

\* cited by examiner

METHOD AND APPARATUS FOR MEASURING CONTRACTION CHARACTERISTICS OF ENGINEERED HEART TISSUE CONSTRUCTS

This application is a U.S. National Stage Filing under 35 U.S.C. 371 from International Application No. PCT/EP2014/055981, filed on Mar. 25, 2014, and published as WO 2014/154704 A1 on Oct. 2, 2014, which claims the benefit of priority under 35 U.S.C. § 119 to European Patent Application No. 13160816.8, filed on Mar. 25, 2013, which are hereby incorporated by reference herein in their entireties.

FIELD OF THE INVENTION

The invention is directed to a novel method for measuring contraction characteristics of engineered heart tissue constructs which is based on the mechanical coupling of the construct to a support element which comprises or is mechanically coupled to a piezoelectric element. An apparatus for carrying out the method of the invention is also provided.

BACKGROUND OF THE INVENTION

Myocardial infarction and heart failure represent the main cause of death in industrialized countries. The loss of terminally differentiated cardiac myocytes which is associated with these pathologies accounts for a decrease in myocardial function which can lead to total organ failure or trigger compensatory mechanisms like hypertrophy of the remaining myocardium and activation of neurohumoral systems.

It has been shown that endogenous regenerative mechanisms do not suffice to compensate for cardiac myocyte death after myocardial infarction. Modern pharmacotherapy can delay, but not reverse the natural course of the disease. Thus, exogenous regenerative strategies including cardiac implantation or the coronary transfusion of cells have been widely discussed in recent years. For example, cells of various origins and developmental stages have been grafted into healthy and diseased hearts, including immature cardiac myocytes, skeletal myoblasts, fibroblasts, endothelial cells, embryonic stem cell-derived cardiac myocytes, and a number of potential cardiac progenitors from peripheral blood or bone marrow. Even though evidence for the formation of true cardiac muscle tissue, electrically coupled to the host myocardium is sparse, some studies reported procedure-induced improvement of contractile function after myocardial infarction.

A more promising concept in cardiac regeneration resides in the ex vivo preparation of 3-dimensional contractile constructs by tissue engineering. Such constructs, which are commonly referred to as engineered heart tissue (EHT) in the literature, can be tailored in size, shape and function before implanting them into the body. In theory, the use of contractile EHT allows for a complete replacement of diseased myocardium or the reconstitution of missing cardiac structures.

Apart from their clinic application, engineered heart tissue constructs may serve as in vitro models for predictive toxicology and target validation. Such EHT-based models take advantage of a particularly physiological cellular environment.

Over the past decade, a number of techniques have been developed to generate cardiac tissue-like constructs in vitro using either neonatal rat heart cells or embryonic stem cells as a starting material (Eschenhagen & Zimmermann (2005); Circ Res.; 97:1220-1231). For example, recent cardiac tissue engineering approaches include the use of solid, preformed scaffolds (Carrier et al. (1999), Biotechnol Bioeng., 64:580-589; Engelmayr et al. (2008), Nat Mater., 7:1003-1010; Li et al. (2000), J Thorac Cardiovasc Surg., 119:368-375; Leor et al. (2000), Circulation, 102 (19 Suppl 3):III-56-III-61); Radisic et al. (2004), Proc Natl Acad Sci USA, 101:18129-18134; Ott et al. (2008), Nat Med., 14:213-221) and matrix-free generation of tissues from stackable cell sheets (Shimizu et al. (2002), Circ Res., 90:e40).

A technique that has attracted considerable attention in the past is the generation of constructs in preformed casting molds using hydrogels such as collagen I, Matrigel, fibronectin, or fibrin (Eschenhagen et al. (1997), FASEB J, 11:683-694; Zimmermann et al. (2002), Circ Res., 90:223-230, Naito et al. (2006), Circulation, 114 (1 Suppl):1-72-1-78; Huang et al. (2007), J Biomed Mater Res A, 80:719-731; Bian et al. (2009), Nat Protoc., 4:1522-1534).

In a recent publication, a simple and robust protocol for generating EHTs from human embryonic stem cells was described (Schaaf et al. (2011), PLoS One, 6(10):e26397. This protocol allows for the preparation of fibrin-based EHTs in a 24-well format using an unselected population of differentiated human embryonic stem cells. Briefly, human embryonic stem cells were differentiated in serum containing media yielding beating embryoid bodies. The embryoid bodies were enzymatically dispersed, and dissociated cells were mixed with fibrinogen and thrombin and poured into slit-formed agarose casting molds. EHT beating activity occurred after 5-10 days.

However, to effectively repair myocardial infarctions or heart defects, EHTs need to be engineered with contractile features that lend significant support to the failing heart tissue in the patient. For this reason, the ability to precisely assess the contraction characteristics of an EHT construct is of utmost importance in preparation of tissue implantation into a patient.

Likewise, drug screening platforms and toxicology models that make use of EHTs are based on monitoring the change in the contraction characteristics of the tissue constructs upon contact with potential drugs and toxic compounds. Thus, it is a prerequisite that the contractile force generated by an EHT can be reliably determined in such screening platform or toxicology model.

At present, two different approaches for the assessment of EHT contraction are known in the art. In the first approach, contractile forces are measured in an organ bath that is equipped with a force transducer (Eschenhagen et al. (1997), FASEB J, 11(8):683-94). This method initially requires the manual fixation of the EHTs to force transducers. The fixed EHT is subsequently immersed in an organ bath filled with an electrolyte solution. This approach is laborious and error-prone. Also, due to the necessity to fix the EHTs manually, the method does not allow to analyze a high number of EHTs at the same time. In addition, EHTs that have been tested in the organ bath can no longer be used for implantation due to sterility constraints.

The second commonly used approach for determining EHTs contraction involves optical surveillance systems (Hansen et al. (2010), Circ. Res., 107(1):35-44). Compared to organ bath measurements, optical surveillance systems can be considered as an improvement. However, this approach still does not allow the simultaneous analysis of a high number of EHTs and is therefore unsuitable for multiplex testing. This is because a video camera can only record a single EHT at a defined point in time. Another disadvantage resides in the generation of a high volume of data. More importantly, however, the evaluation of the contractile force in optical surveillance systems is indirectly achieved measuring the deflection of elastic holdings. In other words, optical surveillance systems require an auxotonic muscle contraction, while the generation of contractile force in heart tissue is normally measured isometrically, i.e. force generation without shortening of the muscle.

Therefore, it is an object of the present invention to provide a method that allows the direct and continuous measurement of contractile characteristics of EHT constructs of different size and geometry. The method should be cost-effective and less laborious than the presently used methods. Ideally, the method should also be amenable to automation and multiplex testing.

This object is achieved by a method having the features of claim 1 and by an apparatus having the features of claim 7. Advantageous embodiments of the method and apparatus are the subject-matter of the respective dependent claims.

According to the present invention a method for measuring contraction characteristics of engineered heart tissue constructs comprises providing one or more engineered heart tissue constructs and attaching each of these engineered heart tissue constructs to a separate first support element, e.g. by mechanically coupling, mounting, adhering or otherwise connecting the respective engineered heart tissue construct to the respective first support element. Thus, in the case of more than one engineered heart tissue construct, the same number of first support elements is used and each engineered heart tissue construct is coupled to a different one of the first support elements. As will become evident later-on, the term "support element" is used to indicate that such an element supports an engineered heart tissue construct during the measurement.

As used herein, engineered heart tissues are three dimensional, contractile, force-generating tissue structures. The engineered heart tissue constructs, which shall be analyzed in terms of their contraction characteristics, can be prepared in accordance with methods and protocols which are known in the art.

According to a preferred embodiment of the present invention, the engineered heart tissue constructs for use in the method of the present invention have been prepared in pre-formed casting molds using solubilised scaffold material, such as collagen I, fibronectin or fibrin. Methods for casting engineered heart tissue constructs using solubilised scaffold material are known in the art and have been described in a number of publications.

For example, Zimmermann et al. (2002), Circ Res 90, 223-30 discloses the generation of engineered heart tissue rings from cardiac myocytes of neonatal rats. The constructs are made from a liquid cell matrix-mixture composed of neutralized, liquid collagen type I, extracellular matrix proteins (Matrigel®), and freshly isolated heart cells from neonatal rats. This reconstitution mixture is pipetted into ring-shaped molding devices. After solidification, engineered heart tissue rings are obtained which start to contract spontaneously. Hansen et al. (2010), Circ Res, 107(1):35-44 describes the generation of heart muscle strips from neonatal rat cells using a fibrin-based hydrogel and Matrigel® in agarose casting molds having a strip format. It was found that tissue constructs prepared based on fribrin or fibrinogen were easier to miniaturize as smaller cell numbers are required compared to collagen-based constructs.

Schaaf et al. (2011), PLoS One, 6(10):e26397 disclose the preparation of strip-shaped engineered heart tissue constructs from human embryonic stem cells. Stem cells are first differentiated to cardiac myocytes by culturing them in the presence of a mixture of growth factors. After enzymatic dissociation, the cells are mixed with fibrin and thrombin and poured into slit-formed agarose casting molds in which two elastic silicone posts were inserted from above. After fibrin polymerisation, the cells were maintained under standard cell culture condition until the onset of contraction.

The engineered heart tissue constructs for use in the method of the present invention can be prepared in accordance with one of the above methods. After the constructs have formed, they can be manually transferred to an apparatus as described below for measuring their contraction characteristics. For this purpose, engineered heart tissue constructs that have been isolated from cell culture medium are attached to the separate first support element.

It is, however, particularly preferred that the engineered heart tissue constructs are grown in place on the support elements. In this case, providing an engineered heart tissue construct and attaching it to a support element occurs generally at the same time. Thus, the step of providing one or more engineered heart tissue constructs and the step of attaching each of these engineered heart tissue constructs to a separate first support element may in fact constitute a single step carried out simultaneously. As described in more detail later on, the engineered heart tissue constructs are preferably prepared using casting molds which are arranged such that the tissue construct is grown directly in contact with the first support element. For example, a strip-shaped casting mold can be positioned such that the first support element and, optionally, the associated second support element extend downwardly into the casting mold. A liquid reconstitution mixture is poured into the casting mold such that the one or more support elements are immersed into the liquid. Upon solidification of the reconstitution mixture, an engineered heart tissue construct is formed around the one or more support elements. When using casting molds into which first and associated second support elements are inserted from above, engineered heart tissue constructs are obtained which are suspended on and between the respective first and second support elements.

Each such first support element to which an engineered heart tissue construct is attached or coupled comprises or is mechanically coupled to at least one piezoelectric element which is the sensing element of a piezoelectric transducer. Thus, the piezoelectric element is a part of the first support element or is provided as a separate element mechanically coupled thereto in such a manner that the below functions can be fulfilled. In this regard, it is preferred that the piezoelectric element is a part of the first support element, and in that case it is even possible that the first support element is constituted by the piezoelectric element. However, it is preferred that the first support element also comprises other parts or elements, e.g. in order to facilitate coupling to an engineered heart tissue construct, to protect the piezoelectric element from environmental influences or for mechanical or stability reasons.

In any case, the attachment, such as the mechanical coupling, of each of the one or more engineered heart tissue constructs to its associated first support element is effected in such a manner that upon contraction—and relaxation—of the respective engineered heart tissue construct a load or force is transferred to the piezoelectric element of the respective first support element and the respective piezoelectric transducer generates and outputs a corresponding electrical sensor signal characteristic of the load or force and/or of a change of the load or force applied to the respective first support element by the respective engineered heart tissue construct due to the contraction—and preferably also expansion—thereof. In other words, the piezoelectric element is chosen and arranged suitably on or in the first support element, the attachment, such as the mechanical coupling, is established at a suitable location, and the engineered heart tissue construct is oriented suitably, such that upon contraction—and expansion—a load or force transfer takes place which induces a corresponding sensor signal indicative of the contraction—and expansion. Consequently, the type and arrangement of the piezoelectric element and the attachment of an engineered heart tissue construct must be adapted to each other. Generally, piezoelectric elements respond to compressive loads. In this connection it should be noted that it is generally difficult or at least more difficult to measure static loads or forces with piezoelectric elements and transducers. This is because applying a load or force to a piezoelectric element results in the accumulation of electrical charge on surfaces of the piezoelectric element, and without taking special measures, this charge will quickly dissipate when attempting to measure the amount of charge accumulated. Thus, while it is in principle possible to measure static loads or forces, it is preferred to measure dynamic loads or forces, i.e. the changes of loads or forces over time. Such changes result in changes in the accumulated charge, which can be continuously measured in a simple manner as electrical currents which change over time. In the case of engineered heart tissue constructs the measurement of the change of the load or force effected by the engineered heart tissue constructs is advantageously possible, because they continuously carry out contraction and expansion cycles.

Finally, for each of the engineered heart tissue constructs, the corresponding sensor signal generated by the respective piezoelectric transducer is analyzed, and at least one contraction characteristic of the engineered heart tissue construct is derived on the basis of the analysis. Contraction characteristics which can be derived from the sensor signals include, e.g., contraction force, contraction frequency, contraction velocity, relaxation velocity, contraction time, relaxation time.

This method has the advantage that the amount of data produced is significantly smaller than the amount of data produced by prior art methods. Therefore, the data analysis and the determination of contraction characteristics is greatly facilitated and can be carried out in less time and with less hardware and work costs. At the same time, the method allows for easily measuring in real time and continuously multiple engineered heart tissue constructs at the same time and over extended periods of time of up to several months. Further, it is advantageously possible to measure engineered heart tissue constructs of different geometries, such as, e.g., strip-shaped, ring-shaped or patch-shaped.

In a preferred embodiment the attachment, e.g. the mechanical coupling, of each of one or more engineered heart tissue construct to a separate first support element comprises, for each of the engineered heart tissue constructs, attaching the respective engineered heart tissue construct to one, two, three, four or more second support elements. For attaching an engineered heart tissue construct to a second support element the same details apply as noted above for attachment to a first support element, i.e. attachment may be effected e.g. by mechanically coupling, mounting, adhering or otherwise connecting the respective engineered heart tissue construct to the respective second support element or by growing the respective engineered heart tissue construct in place onto the respective second support element. Each such second support element is spaced—preferably in its entirety, but at least with a portion thereof—from the associated first support element. Preferably, the space between said at least one first support element and said at least one second support element is between 5 and 50 mm, more preferably between 10 and 25 mm, so that the engineered heart tissue which is formed between these elements has a length in this range. It is particularly preferred that the space between said at least one first support element and said at least one second support element is between 10 and 12 mm. When using a reconstitution mixture as described above, this will result in constructs having an initial length in said range. Upon solidification and further cultivation of the constructs, cells spread inside the matrix and remodel the structure of the construct by the formation of cell-cell-contacts. This usually leads to a condensation of the construct and imposes a mechanical load which bends the support elements toward each other. The condensed constructs will have a length between 6-8 mm which renders them suitable for being used in a multi-well as described herein.

The arrangement of the associated first and second support elements with respect to each other and the mechanical coupling of an engineered heart tissue construct to them is chosen such that each second support element engages the engineered heart tissue construct at a location spaced from the location at which the associated first support element engages the engineered heart tissue construct. In this manner, the engineered heart tissue construct is then supported between the first support element and the associated one or more second support elements, possibly in a stretched state. This is a particularly simple way for ensuring a reliable coupling and a suitable and reliable load or force transfer to the piezoelectric element.

In a further preferred embodiment each of the first support elements is attached to and extends from a base element, which may be provided, e.g., in the form of a frame and/or plate and may be constituted by a printed circuit board. Such base element is then arranged or oriented such that each of the first support elements extends downwardly from the base element while carrying out the measurement. As will become apparent later-on, this advantageously allows for disposing the engineered heart tissue construct(s) in a container or well while the base element is supported at an edge or surrounding region of the opening of the container or well.

For, inter alia, the latter reason, if the preceding two embodiments are combined, it is preferred that each of the second support elements is attached to and extends from the base element such that, when said base element is arranged such that each of the first support elements extends downwardly from the base element, each of the second support elements likewise extends downwardly from the base element. In this orientation each of the engineered heart tissue constructs is suspended on and between the associated first and second support elements.

In any embodiment comprising arranging the base element such that the one or more first support elements and—if present—the one or more second support elements extend downwardly therefrom, it is advantageous to arrange the base element on the surface of a suitably dimensioned multi-well plate such that each of the first support elements together with—if present—its associated second support element(s) extends downwardly from the base element in a different one of the wells of the multi-well plate. In this case, the engineered heart tissue constructs are attached, e.g. mechanically coupled, to the first and second support elements such that each is arranged in a different one of the wells. It is then possible to carry out the measurements in culture media, in order to maintain the engineered heart tissue constructs functional, or in different selected media in order to study their impact on the contraction characteristics.

In embodiments utilizing one or more second support elements, each of the first support elements is preferably rigid, and then, for example, the following measurements can be carried out:

a) For one or more or all of the first support elements all of the respective associated one or more support elements may be selected to be rigid, so that the respective engineered heart tissue construct carries out an isometric contraction on the respective first and second support elements with no or only little deformation thereof.

b) For one or more or all of the first support elements one or more or all of the respective associated second support elements may be selected to be flexible, so that the respective engineered heart tissue construct carries out an auxotonic contraction on the respective first and second support elements while bending the flexible second support elements. Of course, in case for a first support element the associated second support elements comprise rigid as well as flexible second support elements, the flexible second support elements must be suitably located to allow deformation thereof upon contraction of the engineered heart tissue construct.

c) For one or more or all of the first support elements one or more or all of the respective associated second support elements may be selected such that they can be selectively configured to assume (i.e. switched between) a rigid state and a flexible state. These second support elements are then changed between their rigid and flexible states, and for the respective engineered heart tissue constructs isometric and auxotonic contraction are measured at different times depending on the state of the corresponding second support elements. Further, it is easily possible to adapt a measurement arrangement to different applications. For each state the considerations indicated above for the first two cases apply.

In this regard, it is possible to combine the different possibilities, e.g. by providing that for some first support elements the associated second support elements are rigid and for others of the first support elements the associated second support elements are flexible.

The above-described method can be advantageously carried out by an apparatus comprising a base element and one or more first support elements, each attached to and extending from the base element. For the base element and the first support elements all of the above explanations and details apply. Thus, in particular, each such first support element comprises or is mechanically coupled to at least one piezoelectric element which is the sensing element of a piezoelectric transducer, i.e. the piezoelectric element is a part of the first support element or is provided as a separate element mechanically coupled thereto in such a manner that the functions mentioned below and above can be fulfilled. In this regard, it is preferred that the piezoelectric element is a part of the first support element, and in that case it is even possible that the first support element is constituted by the piezoelectric element. However, it is preferred that the first support element also comprises other parts or elements, e.g. in order to facilitate coupling to an engineered heart tissue construct, to protect the piezoelectric element from environmental influences or for mechanical or stability reasons.

Further, each of the first support elements comprises a support portion adapted for attaching an engineered heart tissue construct thereto. It should be noted that in case a first support element is suitable for attaching an engineered heart tissue construct thereto at an arbitrary location, the support portion may simply be constituted by the entire first support element or by an arbitrary portion of the first support element. However, even in that case it is preferred that the first support elements comprises a predetermined portion as support portion, which may be, e.g., marked or specifically constructed for facilitating attachment, so that in operation engineered heart tissue constructs can be attached to the first support elements at defined locations thereof. Further, as also already briefly indicated above, the type and arrangement of the piezoelectric element with respect to the respective first support element and the location and configuration of the support portion are chosen such that after attaching an engineered heart tissue construct to the support portion the respective engineered heart tissue construct can be arranged and stabilized in such a manner that upon contraction thereof a load or force is transferred to the respective piezoelectric element and the respective piezoelectric transducer generates and outputs a corresponding electrical sensor signal characteristic of the load or force applied to the respective first support element by the respective engineered heart tissue construct due to the contraction thereof.

The use and operation of this apparatus can be taken from the above description of the method.

In the following some preferred embodiments are described which are specifically adapted to corresponding ones of the above preferred embodiments of the method. The use, operations and advantages can be taken from the corresponding portions of the above description.

In a preferred embodiment the apparatus further comprises, for each of the one or more first support elements, one or more second support elements attached to and extending from the base element. Each such second support element comprises a support portion adapted for attaching an engineered heart tissue construct thereto. Again, it should be noted that in case a second support element is suitable for attaching an engineered heart tissue construct thereto at an arbitrary location, the support portion may simply be constituted by the entire second support element or by an arbitrary portion of the second support element. However, even in that case it is preferred that the second support elements comprises a predetermined portion as support portion, which may be, e.g., marked or specifically constructed for facilitating attachment, so that in operation engineered heart tissue constructs can be attached to the second support elements at defined locations thereof. Further, each such support portion of each such second support element is spaced from and arranged with respect to the support portion of the respective first support element, such that, after attaching an engineered heart tissue construct to the support portion of one of the first support elements and to the support portion of each respective associated second support element, the respective engineered heart tissue construct is engaged by the support portion of the respective first support element at a location spaced from the location at which the support portion of each of the respective associated second support elements engage the engineered heart tissue construct, so that it is supported, preferably in a stretched state, between the respective first support element and the respective second support elements. In particular, it is preferred that each of the second support elements is entirely spaced from the associated first support element.

In this embodiment it is further preferred that each of the first support elements and each of the second support elements extend from a same side of the base element, and that the base element is adapted to be disposed on the surface of a suitably dimensioned multi-well plate, such that each of the first support elements extends, together with its associated second support elements, into a separate one of the wells of the multi-well plate. The support portions of the first and second support elements are then arranged and located such that each engineered heart tissue construct attached to the support portions of one of the first support elements and the associated second support elements is suspended on and between the respective first and second support elements and disposed inside the respective one of the wells of the multi-well plate.

In this embodiment it is further preferred that each of the first support elements is rigid, and that a) for at least one of the first support elements all of the associated second support elements are rigid, so that engineered heart tissue constructs attached to the support portions of one of these first support elements and the associated second support elements carry out an isometric contraction on the respective first and second support elements, b) for one or more or all of the first support element one or more or all of the associated second support elements are flexible, so that engineered heart tissue constructs attached to the support portions of one of these first support elements and the associated second support elements carry out an auxotonic contraction on the respective first and second support elements, and/or c) for one or more or all of the first support elements one or more or all of the associated second support elements are selectively configurable to assume a rigid state and a flexible state, so that engineered heart tissue constructs attached to the support portions of these first support elements and the associated second support elements carry out isometric or auxotonic contraction, depending on the state of the respective second support elements.

Again, these possibilities can be combined. For example, mixing cases a) and b), isometric and auxotonic measurements can be carried out using different first support elements. Case c) is even more flexible, because it provides both possibilities in various freely selectable configurations.

If case c) is realized in the above embodiment, it is preferred that the corresponding second support elements each comprise a flexible elongate tubular element—e.g. made of silicone—and a rigid elongate element shaped and dimensioned to be selectively inserted into and removed from the tubular element for selectively configuring the respective second support element to be flexible and rigid. This is a particularly simple and reliable construction of such second support elements.

In a preferred embodiment the support portions of the first and—if present—second support elements comprise or are made of silicone. However, such support portions may also comprise or be made of other flexible, bio-compatible materials. Additionally or alternatively the support portions may comprise or be a region of increased surface roughness as compared to the remainder of the respective support element.

In a preferred embodiment, which may be advantageously combined with the preceding embodiment, each of the first support elements comprises an elongate section extending from the base element, and the respective support portion is preferably located at or near the longitudinal end of the elongate section remote from the base element. In this case it is particularly preferred if the support portion comprises or is a portion extending transversely and, more preferably, perpendicularly with respect to the elongate section to opposite sides of the elongate section. In this regard it should be noted that in addition to such a portion extending transversely or perpendicularly with respect to the elongate section to opposite sides thereof the support portion preferably also comprises a portion of the elongate section immediately adjacent to the transversely or perpendicularly extending portion. If the apparatus is arranged such that the elongate section extends downwardly from the base element, an engineered heart tissue construct may then advantageously be looped or grown around the elongate section adjacent to the transversely or perpendicularly extending portion (and preferably also around the transversely or perpendicularly extending portion) such that the transversely or perpendicularly extending portion prevents the engineered heart tissue construct from slipping from the elongate section and the respective support element. If the engineered heart tissue construct adheres to the elongate section, the transversely or perpendicularly extending portion constitutes an additional securing means. In any case, the elongate section, which is preferably straight, may be, e.g., bar- or strip-shaped. The transversely or perpendicularly extending portion of the support portion may be advantageously, e.g., disk-, plate-, dish- or bar-shaped. A disk-, plate- or dish-shaped transversely or perpendicularly extending portion, resulting in, e.g., a generally mushroom-shaped configuration of the first support element with the foot of the "mushroom" being connected to the base element, may be used for relatively weak engineered heart tissue constructs, whereas a bar-shaped portion extending transversely or perpendicularly with respect to the elongate section may be used for relatively strong engineered heart tissue constructs. In the latter case the first support element may, in particular, be chosen to have a T-shaped configuration, with the base of the "T" being connected to the base element.

In a preferred embodiment, which may be advantageously combined with either one or both of the two preceding embodiments, each of the second support elements comprises an elongate section extending from the base element, and the respective support portion is preferably located at or near the longitudinal end of the elongate section remote from the base element. Also in this case it is particularly preferred if the support portion comprises or is a portion extending transversely and, more preferably, perpendicularly with respect to the elongate section to opposite sides of the elongate section. In this regard it should be noted that in addition to such a portion extending transversely or perpendicularly with respect to the elongate section to opposite sides thereof the support portion preferably also comprises a portion of the elongate section immediately adjacent to the transversely or perpendicularly extending portion. If the apparatus is arranged such that the elongate section extends downwardly from the base element, an engineered heart tissue construct may then advantageously be looped or grown around the elongate section adjacent to the transversely or perpendicularly extending portion (and preferably also around the transversely or perpendicularly extending portion) such that the transversely or perpendicularly extending portion prevents the engineered heart tissue construct from slipping from the elongate section and the respective support element. If the engineered heart tissue construct adheres to the elongate section, the transversely or perpendicularly extending portion constitutes an additional securing means. In any case, the elongate section, which is preferably straight, may be, e.g., bar- or strip-shaped. The transversely or perpendicularly extending portion of the support portion may be advantageously, e.g., bar-, disk-, dish- or plate-shaped. If it extends transversely or perpendicularly with respect to the elongate section, the second support element may, in particular, be chosen to have a T-shaped or mushroom-shaped configuration, with the foot of the "T" or "mushroom" being connected to the base element. In the case of a strong engineered heart tissue construct choosing a T-shaped configuration with a support portion being or comprising a bar-shaped portion may be suitable. However, in the case of the second support elements it is preferred to account for the strength of the engineered heart tissue construct by using more or less second support elements.

In a preferred embodiment each of the piezoelectric transducers is electrically connected to electronic circuitry integrated into or disposed on the base element and adapted for conditioning, converting, processing and/or analyzing the respective sensor signals. In this regard, in case of multiple piezoelectric transducers a single electronic component or circuit may be electrically connected to all piezoelectric transducers, or separate electronic circuitry, which may or may not be interconnected, may be electrically connected to different ones of the piezoelectric transducers. In any case, it is particularly preferred that the base elements is or comprises a printed circuit board on which the circuitry is provided and to which the first and—if present—second support elements are attached. Providing the electronic circuitry on the base element ensures short signal paths and, consequently, fast response times and reduced noise and interference.

In a preferred embodiment one or more or all of the first support elements comprise at least one strain gauge mechanically coupled to the respective first support element, such that after attaching an engineered heart tissue construct to the support portion of the respective first support element the engineered heart tissue construct can be arranged such that upon contraction thereof a load is transferred to the respective at least one strain gauge and the respective at least one strain gauge generates and outputs a corresponding electrical strain gauge signal characteristic of the static load applied by the respective engineered heart tissue construct to the respective first support element due to the contraction thereof. Such strain gauges may likewise be coupled to electronic circuitry of the type and arrangement mentioned above. Although strain gauges have a rather low sensitivity as compared to the piezoelectric transducers, they can be advantageously combined therewith in order to also provide for measurements of static force characteristics of the engineered heart tissue constructs.

In the following an embodiment of the invention will be explained in more detail with reference to the drawings, in which.

Figure 1:
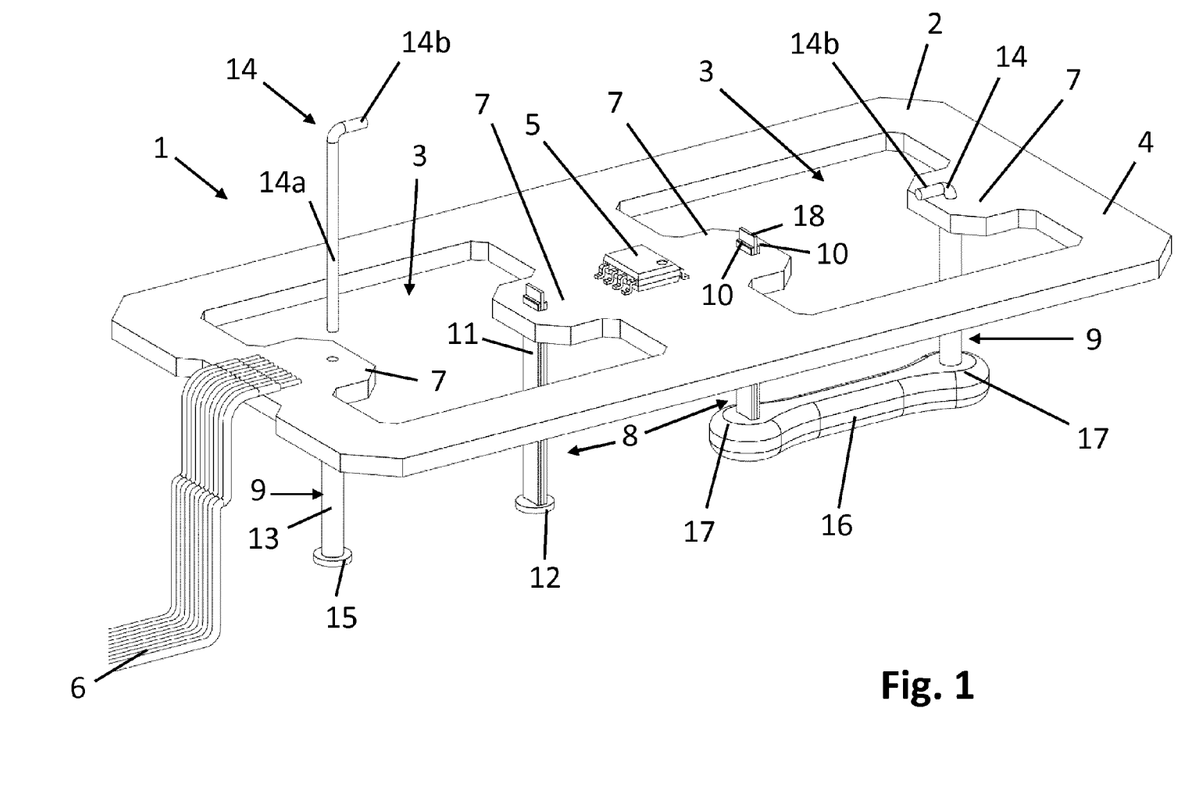
FIG. 1 is a perspective view of an apparatus according to an embodiment of the invention, wherein an engineered heart tissue construct is attached thereto in a measurement position.

The apparatus 1 shown in FIG. 1 comprises a planar plate-shaped base element 2 having two generally rectangular cutouts 3. On the, in FIG. 1, upper surface 4 of the base element 2 electronic circuitry comprising an integrated circuit component 5 as well as a flexible strip 6 including electrical conduits are mounted. The component 5 is located between the two cut-outs 3. As will be described below, the component 5 is coupled to different piezoelectric transducers in order to process their signals, and is also coupled to the electrical conduits of the strip 6 in order to provide the processed signals to exterior means. In this regard, it is advantageous if the base element 2 is a printed circuit board and signal conduction to and from the component 5 is effected by means of conductive traces (not shown) of the printed circuit board 2.

From two opposite edges of each of the cut-outs 3 a projection 7 extends into the cut-out 3 in the same plane with the remainder of the base element 2. To each of the projections 7 a straight, elongate support element 8, 9 is attached such that the support elements 8, 9 extend downwardly for the, in FIG. 1, lower surface of the base element 2 in a manner perpendicularly to the plane defined by the base element 2. In this regard, for each of the cut-outs 3 one of the projections 7 carries a support element 8 and the other projection 7 carries a support element 9, so that overall two support elements 8 of identical construction and two support elements 9 of identical construction are present. The two support elements 8 are attached to the projections 7 closest to the component 5.

Each support element 8 comprises two strip shaped piezoelectric elements 10 sandwiching between them an intermediate layer 18 stabilizing the piezoelectric elements 10 and possibly providing support for electrical conduits and/or circuitry operatively coupled to the piezoelectric elements 10. This sandwich structure forms an elongate section 11, to the longitudinal end of which remote from the respective projection 7 a dish-shaped silicone element 12 having a circular shape and extending perpendicularly to the direction of extension of the elongate section 11 is attached. The element 12 has rounded edges. For protecting the piezoelectric elements 10 against external influences, the entire elongate section 11 or at least the piezoelectric elements 10 may be provided with a protective coating (not shown). Preferably, the piezoelectric elements 10 are electrically connected in series in order to provide together a signal which is twice the signal of a single piezoelectric element 10. In this manner, the sensitivity is increased without increasing the length of the elongate sections 11 and the support elements 8.

On the other hand, each support element 9 comprises a straight elongate silicone tube 13 of circular cross-section and a cylindrical elongate rod 14, which is rigid and also of circular cross-section. Each such rod 14 comprises a straight section 14a, which extends over nearly the entire length or at least most of the length of the rod 14, and at one of its longitudinal ends an end section 14b bent by 90° as compared to the straight section 14a. The rod 14 is dimensioned such that the rod 14 or, more particularly, the straight section 14a thereof can be selectively inserted into and removed from the tube 13 to selectively render the support element 9 rigid and flexible, respectively. In this regard, the length of the rod 14 and of the straight section 14a thereof are chosen to be greater than the length of the tube 13, to allow for rendering the support element 9 rigid along the entire length of the tube 13 while being able to easily remove the rod 14 when flexibility of the support element 9 is desired. Further, the diameter of the rod 14 is chosen such that insertion and removal are possible, but sufficient rigidity in the radial direction is also provided. The bent end section 14b provides the advantage that the protrusion of the rod 14 above the base element 2 is limited, so that the entire arrangement is kept relatively flat, even if covered with a lid. However, in principle it is also possible that the rods 14 are straight along their entire length, i.e. that the bent section 14b is omitted.

To the longitudinal end of the tube 13 remote from the respective projection 7 a dish-shaped silicone element 15 having a circular shape and extending perpendicularly to the direction of extension of the tube 13 is attached. The element 15 has rounded edges and, in the example illustrated, is identical to the elements 12. All elements 12 and 15 are arranged at the same distance from the base element 2.

For each of the support elements 8 the piezoelectric element 10 forms, together with electrical components not specifically shown, a piezoelectric transducer which is, in turn, electrically connected to the component 5. The support elements 8 are arranged as close as possible to the component 5 in order to keep noise, interference and response time at a minimum.

The elements 12 and 15 constitute support portions which are suitable for attaching engineered heart tissue constructs thereto. More particularly, each pair of support elements 8 and 9 associated with the same cut-out 3 is adapted and intended for mounting an engineered heart tissue construct to the corresponding pair of support elements 12 and 15. If the support portions 12 and 15 are immersed into a liquid reconstitution mixture which is provided in a rectangular casting mold, the strip-shaped engineered heart tissue construct formed upon solidification directly attaches to the support elements 8 and 9 via the corresponding support portions 12 and 15. This is illustrated for an engineered heart tissue construct 16 for the rightmost pair of support elements 8 and 9. As illustrated, it is suspended in a slightly stretched state between the two support elements 8 and 9, wherein the tissue has attached to the support portions 12 and 15 at contact points 17. The dish-shaped support elements 12, 15 prevent that the engineered heart tissue construct slips off the support elements 8 and 9 upon culturing of the construct.

In FIG. 1 the rod 14 is inserted into the tube 13, so that the support element 9 carrying the engineered heart tissue construct 16 is rigid. Thus, upon contraction of the engineered heart tissue construct 16 the support element 9 remains in the shown configuration. The same essentially applies to the support element 8. However, due to the sandwich structure and overall strip-shaped configuration of the elongate section 11, it slightly deforms together with the piezoelectric element 10. Due to the high sensitivity thereof, a small deformation, which is invisible in practice, is sufficient for the piezoelectric transducer to generate a signal indicative of the force changes applied by the engineered heart tissue construct 16 to the support element 8. This configuration measures isometric contraction of the engineered heart tissue construct 16.

When the rod 14 is removed from the tube 13, contraction of the engineered heart tissue construct 16 results in bending of the support element 9. Nevertheless, the sensitivity of the piezoelectric transducer is so high that a signal indicative of the force applied by the engineered heart tissue construct 16 to the support element 8 is generated. This configuration measures auxotonic contraction of the engineered heart tissue construct 16.

As should be evident from the preceding explanations, in this embodiment the support elements 8 constitute first support elements in accordance with the above general description, the support elements 9 constitute second support elements in accordance with the above general description, and the elements 12 and 15 constitute corresponding support portions in accordance with the above general description.

Figure 2:
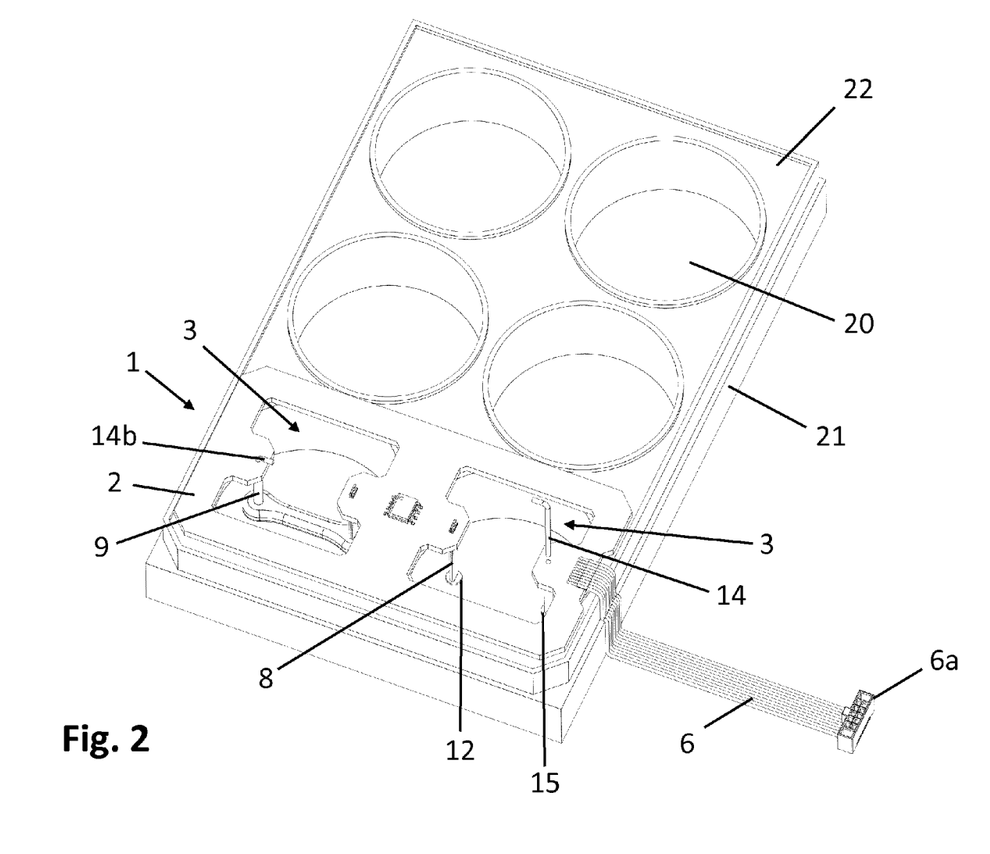
FIG. 2 is a perspective view of the apparatus of FIG. 1 being supported on a multi-well plate.

FIG. 2 shows in which manner the apparatus 1 may be advantageously used for measuring while two engineered heart tissue construct 16 mounted to the two pairs of support elements 8 and 9 are disposed inside two different wells 20 of a suitably dimensioned multi-well plate 21.

The dimensions of the multi-well plate 21 are adapted to the apparatus 1, such that the distance between the centers of the two cut-outs 3 is identical to the distance between the centers or longitudinal axes of two adjacent wells 20, that the distance between the two support elements 8, 9 associated with each cut-out 3 is smaller than the diameter of the wells 20, and that an engineered heart tissue construct 16 suspended on the elements 12 and 15 is spaced from the bottom of the well 20 if the base element 2 is located on the surface 22 of the multi-well plate 21 extending between the openings of the wells 20 and the two pairs of support elements 8 and 9 extend into adjacent ones of the wells 20.

In this arrangement of the apparatus 1 on the multi-well plate 21, the flexible strip 6 including electrical conduits can be conveniently guided around the multi-well plate 21 and comprises a connector 6a for connection to external devices. The cut-outs 3 allow visual inspection of the engineered heart tissue constructs 16 without moving the apparatus 1.

In the measurement position shown in FIG. 2, the apparatus 1 may be covered during the measurement by a, preferably transparent, lid. When using rods 14 with a bent end section 14b, the apparatus 1 advantageously adds only little to the height of the multi-well plate 21.

As mentioned above, the apparatus of the invention may be used in combination with casting molds to prepare engineered heart tissue constructs based on a liquid reconstitution mixture. The apparatus can be arranged above the casting molds which contain the liquid reconstitution mixture such that the tips of the downwardly extending support elements are immersed in the reconstitution mixture. Non-limiting examples for protocols for the preparation of engineered heart tissue constructs are provided below. Any other method which has been described in the art for the generation of engineered heart tissue based on liquid reconstitution mixtures can be used as well.

Protocol 1: Tissue Constructs from Rat Cardiac Myocytes

Unpurified heart cells were isolated from neonatal Wistar rats (postnatal day 0 to 3) by a fractionated DNase/Trypsin digestion protocol as previously described (Zimmermann et al. (2000), Biotechnol Bioeng., 68:106-114). The resulting cell population was immediately processed to prepare the tissue constructs.

To generate the engineered heart tissue constructs, a reconstitution mix was prepared on ice as follows (final concentration): $4.1 \times 10^6$ cells/ml, 5 mg/ml bovine fibrinogen (stock solution: 200 mg/ml plus aprotinin 0.5 µg/mg fibrinogen in NaCl 0.9%, Sigma F4753), 100 µl/ml Matrigel (BD Bioscience 356235). 2×DMEM was added to match the volumes of fibrinogen and thrombin stock to ensure isotonic conditions. Casting molds were prepared by placing a teflon spacer in 24-well culture dishes and adding 1.6 ml 2% agarose in PBS (Invitrogen 15510-027) per well. After agarose solidification the spacer were removed (yielding a casting mold of 12×3×4 mm) and silicon post racks were placed onto the dishes with pairs of posts reaching into each casting mold. For each construct 145 µl reconstitution mix was mixed briefly with 4.5 µl thrombin (100 U/ml, Sigma Aldrich T7513) and pipetted into the agarose slot.

For fibrinogen polymerisation the constructs were placed in a 37° C., 7% CO2 humidified cell culture incubator for 2 hours. 300 µl of cell culture medium was then added per well to ease removal of the constructs from agarose casting molds. The racks were transferred to new 24-well cell culture dishes. Constructs were maintained in 37° C., 7% $CO_2$ humidified cell culture incubator. Media was changed on Mondays, Wednesdays and Fridays. The medium consisted of DMEM (Biochrom F0415), 10% horse serum (Gibco 26050), 2% chick embryo extract, 1% Penicillin/Streptomycin (Gibco 15140), insulin (10 µg/ml, SigmaAldrich 19278), tranexamic acid (400 µM, Sigma-Aldrich 857653) and aprotinin (33 µg/ml, Sigma Aldrich A1153).

Directly after casting, the engineered heart tissue constructs contained evenly distributed amorphous round heart cells. Within days, cells elongated, aligned along force lines, and started to beat as single cells at day 4 to 5. Degradation and remodeling of extracellular matrix led to a marked reduction of construct size, increased cellular density, and formation of small groups of cardiac myocytes and, at day 7 to 9, to coherent beating. By day 10, force of contraction was sufficient to rhythmically deflect the posts. Measurements were routinely done between days 14 to 16. At this point of development cardiomyocytes appear as approximately 100 to 200 µm long spindle-shaped cells with maximum diameter of 10 to 20 µm.

Further details of this protocol can be taken from the publication of Hansen et al. (2010), Circ. Res., 107(1):35-44 and the references cited therein.

Protocol 2: Tissue Constructs from Human Embryonic Stem Cells

HES2 cells (HES2.R26, see Irion et al. (2007), Nature Biotechnology 25: 1477-82) were propagated on Matrigel® with CF1-MEF conditioned medium according to the protocol of Xu et al. (2001), Nature Biotechnology 19: 971-4. Confluent layers of hESC colonies were digested with collagenase IV (Gibco 17104, 1 mg/ml, 1 ml/10 cm$^2$) until edges of the colonies start to dislodge (10-20 minutes). Collagenase was removed and washed with 2 ml PBS/10 cm$^2$. CF1-MEF conditioned medium was added (1 ml/10 cm$^2$). Embryoid bodies (EBs) were generated by carefully scraping off colony fragments with a 5 ml-pipette tip. Colony fragments were collected and remaining colonies were detached with a cell scraper. EB formation was performed in ultra low attachment cell culture flasks (ULA-CCF, Corning 3815), with colony fragments of 2.5 cm$^2$ (undifferentiated hESC layer) per ml conditioned medium.

Differentiation was performed in RPMI-B27 medium containing RPMI 1640 (Gibco 21875), B-27 supplement (2%, Gibco 0080085-SA), Penicillin/Streptomycin (0.5%, Gibco 15140) and HEPES (10 mM). Y-27632 (10 mM, Biaffin PKI-27632-010) and growth factors were added. After 24 hours, EBs were collected in 50 ml tubes. ULA-CCFs were washed twice with PBS, solutions were added to the tubes and centrifuged (4 minutes, 300 rpm). Pelleted EBs were resuspended in 20 ml mesodermal induction medium (stage I, basic FGF (5 ng/ml, R&D 233-FB), Activin-A (6 ng/ml, R&D 338-AC), BMP-4 (10 ng/ml, R&D 314-BP), Y-27632 (10 mM)) and transferred back into the ULA-CCF. After 1-3 days EBs were collected in 50 ml tubes. ULA-CCFs were washed twice with PBS, and the solutions were added to the tubes and centrifuged (4 minutes, 300 rpm). EBs were resuspendend in 15 ml cardiomyocyte induction medium (stage II, DKK-1 (150 ng/ml, R&D 5439-DK), VEGF (10 ng/ml, R&D 293-VE), Y-27632 (10 mM) and transferred back into the ULA-CCF. After 3 days EBs were collected in 50 ml tubes. ULA-CCFs were washed twice with PBS, solutions were added to the tubes and centrifuged (4 minutes, 300 rpm). EBs were resuspendend in 15 ml cardiomyocyte induction medium (stage III, DKK-1 (150 ng/ml), VEGF (10 ng/ml), basic FGF (5 ng/ml)).

After 5-7 days 5 ml of RPMI-B27 medium was added every second day until the first beating EBs were detected. EB formation and differentiation was performed at 95% humidity, 37° C., 5% oxygen, 5% CO2. EBs were transferred to serum-containing medium (DMEM, Gibco 41965, 1% L-glutamine, 1% NEAA, 0.5% Penicillin/Streptomycin, 20% fetal bovine serum, 100 mM 2-mercaptoethanol) between day 12-15 and were kept at 20% oxygen. Onset of beating occurred between day 10 and day 15. EBs were dissociated with 500 ml of a pre-warmed mixture (37° C.) of collagenase and trypsin (approximately 1 mg/ml collagenase in 0.5% trypsin solution) for 2-5 minutes under continuous trituration with a 100 ml pipette. Dissociated cells were washed twice by adding 1 ml of serum containing media and centrifugation for 2 min at 200 g.

After cell counting human EHTs were generated according to PROTOCOL 1 described above for neonatal rat cardiomyocytes. Specifically, 0.6×10$^6$ differentiated cells were mixed with fibrinogen and thrombin and poured into slit-formed agarose casting molds in a standard 24-well plate in which two elastic silicone posts per well were inserted from above. After fibrin polymerisation (2 hours) silicone racks with 4 pairs of silicone posts each and the respective cell-fibrin gel were transferred to new 24 well plates and maintained under standard cell culture conditions (37° C., 95% humidity, 40% oxygen). Medium was changed on Mondays, Wednesdays and Fridays. Medium composition was: DMEM (Biochrom F0415), 10% horse serum (Gibco 26050), 2% chick embryo extract, 1%, penicillin/streptomycin (Gibco 15140), insulin (10 mg/ml, Sigma-Aldrich 19278), tranexamic acid (400 µM, Sigma-Aldrich 857653) and aprotinin (33 mg/ml, Sigma-Aldrich A1153). Y-27632 (10 mM was added to the medium for the first 24 hours. EHTs were subjected to contraction analysis after 5 weeks, thus matching the age of 7-8 week old EBs.

Further details of this protocol can be gathered from Schaaf et al. (2011), PLoS One, 6(10):e26397 and the references cited therein.

The invention claimed is:

1. A method for measuring contraction characteristics of engineered heart tissue constructs, comprising the following steps:

providing at least one engineered heart tissue construct, attaching each of said at least one engineered heart tissue construct to a separate first support element, which comprises or is mechanically coupled to a piezoelectric element which is the sensing element of a piezoelectric transducer, such that upon contraction of the respective engineered heart tissue construct a load is transferred to the respective piezoelectric element and the respective piezoelectric transducer generates and outputs a corresponding electrical sensor signal characteristic of the load and/or of a change of the load applied to the respective first support element by the respective engineered heart tissue construct due to the contraction thereof, and analyzing, for each of said at least one engineered heart tissue construct, the sensor signal output by the respective piezoelectric transducer and deriving at least one contraction characteristic of said at least one engineered heart tissue construct on the basis of the analysis, wherein the step of attaching each of said at least one engineered heart tissue construct to a separate first support element comprises, for each of said at least one engineered heart tissue construct, attaching the respective engineered heart tissue construct to at least one second support element, each being spaced with at least a portion thereof from the respective first support element and each engaging the respective engineered heart tissue construct at a location spaced from a location at which the respective first support element engages the respective engineered heart tissue construct, so that it is suspended between the respective first support element and the respective at least one second support element.

2. The method of claim 1, wherein each of the first support elements is attached to and extends from a base element, and wherein the method further comprises the step of arranging said base element such that each of the first support elements extends downwardly from the base element.

3. The method of claim 2, wherein the step of arranging said base element such that each of the first support elements extends downwardly from the base element comprises arranging the base element on the surface of a multi-well plate such that the base element is supported on the surface and each of said at least one engineered heart tissue construct is disposed in a separate one of the wells of the multi-well plate.

4. The method of claim 1, wherein each of the second support elements is attached to and extends from the base element such that, when said base element is arranged such that each of the first support elements extends downwardly from the base element, each of the second support elements likewise extends downwardly from the base element, so that each of said at least one engineered heart tissue construct is suspended on and between the respective first and second support elements.

5. The method claim 1, wherein each of the at least one first support elements is rigid, and wherein
for at least one of the at least one first support element each of the associated at least one second support element is rigid, so that the respective engineered heart tissue construct carries out an isometric contraction on the respective first and second support elements,
for at least one of the at least one first support element at least one of the associated at least one second support element is flexible, so that the respective engineered heart tissue construct carries out an auxotonic contraction on the respective first and second support elements, and/or
for at least one of the at least one first support element at least one of the associated at least one second support element can be selectively configured to assume a rigid state and a flexible state, and the method comprises selectively changing these second support elements between their rigid and flexible state and measuring both isometric and auxotonic contraction of the respective engineered heart tissue constructs.

6. An apparatus for carrying out the method of any of the preceding claims, comprising
a base element, and
at least one first support element attached to and extending from the base element, each of said at least one first support element comprising or being mechanically coupled to a piezoelectric element, which is the sensing element of a piezoelectric transducer,
wherein each of said at least one first support element comprises a support portion adapted for attaching an engineered heart tissue construct thereto, wherein after attaching an engineered heart tissue construct to the support portion the respective engineered heart tissue construct can be arranged such that upon contraction thereof a load is transferred to the respective piezoelectric element and the respective piezoelectric transducer generates and outputs a corresponding electrical sensor signal characteristic of the load and/or of the change of the load applied to the respective first support element by the respective engineered heart tissue construct due to the contraction thereof, and
at least one second support element for each of said at least one first support element, said at least one second support element attached to and extending from the base element, wherein
each of said at least one second support element comprises a support portion adapted for attaching an engineered heart tissue construct thereto, and
each support portion of each second support element is spaced from and arranged with respect to the support portion of the respective first support element, such that, after attaching an engineered heart tissue construct to the support portion of one of said at least one first support element and to the support portion of each associated second support element, the respective engineered heart tissue construct is engaged by the support portion of the respective first support element at a location spaced from the location at which the support portion of each of the respective at least one second support element engages the engineered heart tissue construct, so that it is suspended between the respective first support element and the respective at least one second support element.

7. The apparatus of claim 6, wherein each of said at least one first support element and each of said at least one second support element extend from a same side of the base element, and wherein the base element is adapted to be disposed on the surface of a suitably dimensioned multi-well plate, such that each of said at least one first support element and the associated at least one second support element extends into a separate one of the wells of the multi-well plate, and that each engineered heart tissue construct attached to the support portions of one of said at least one first support element and the associated at least one second support element is suspended on and between the respective first and second support elements and disposed inside the respective one of the wells of the multi-well plate.

8. The apparatus of claim 6, wherein each of the first support elements is rigid, and wherein
for at least one of the at least one first support element each of the associated at least one second support element is rigid, so that engineered heart tissue constructs attached to the support portions of one of these first support elements and the associated at least one second support element carry out an isometric contraction on the respective first and second support elements,
for at least one of the at least one first support element at least one of the associated at least one second support element is flexible, so that engineered heart tissue constructs attached to the support portions of one of these first support elements and the associated at least one second support element carry out an auxotonic contraction on the respective first and second support elements, and/or
for at least one of the at least one first support element at least one of the associated at least one second support element can be selectively configured to assume a rigid state and a flexible state, so that engineered heart tissue constructs attached to the support portions of these first support elements and the associated at least one second support element carry out isometric or auxotonic contraction, depending on the state of the respective at least one second support element.

9. The apparatus of claim 8, wherein, for at least one of the at least one first support element, at least one of the associated at least one second support element is selectively configurable to assume a rigid state and a flexible state, and comprises a flexible elongate tubular element and a rigid elongate element adapted to be selectively inserted into and removed from the tubular element for selectively configuring the respective second support element to be flexible and rigid.

10. The apparatus of claim 6, wherein
the support portions of the first and second support elements comprise or are made of silicone, and/or
each of the at least one first support element comprises an elongate section extending from the base element and the respective support portion is located at the longitudinal end of the elongate section remote from the base element, the support portion comprising a portion extending transversely with respect to the elongate section to opposite sides thereof, and/or
each of the at least one second support element comprises an elongate section extending from the base element and the respective support portion is located at the longitudinal end of the elongate section remote from the base element, the support portion comprising a portion extending transversely with respect to the elongate section to opposite sides thereof.

11. The apparatus of claim 6, wherein each of the piezoelectric transducers is electrically connected to electronic circuitry integrated into or disposed on the base element and adapted for conditioning, converting, processing and/or analyzing the respective sensor signals.

12. The apparatus of claim 6, wherein at least one of the at least one first support element comprises at least one strain gauge mechanically coupled to the respective first support element, such that after attaching an engineered heart tissue construct to the support portion of the respective first support element the engineered heart tissue construct can be arranged such that upon contraction thereof a load is transferred to the respective at least one strain gauge and the respective at least one strain gauge generates and outputs a corresponding electrical strain gauge signal characteristic of the static load applied by the respective engineered heart tissue construct to the respective first support element due to the contraction thereof.

13. The apparatus of claim 6, wherein the distance between said support portion of said at least one first support element and the support portion of the respective at least one second support element is between 5 and 50 mm.

* * * * *

UNITED STATES PATENT AND TRADEMARK OFFICE
CERTIFICATE OF CORRECTION

PATENT NO. : 10,172,712 B2
APPLICATION NO. : 14/780199
DATED : January 8, 2019
INVENTOR(S) : Eschenhagen et al.

Page 1 of 1

It is certified that error appears in the above-identified patent and that said Letters Patent is hereby corrected as shown below:

In the Claims

In Column 17, Line 26, in Claim 5, after "method", insert --of--

In Column 17, Line 48, in Claim 6, after "comprising", insert --:--

Signed and Sealed this
Twenty-first Day of April, 2020

Andrei Iancu
*Director of the United States Patent and Trademark Office*